(12) United States Patent
Iwanaga et al.

(10) Patent No.: US 8,173,271 B2
(45) Date of Patent: May 8, 2012

(54) FLUORESCENT RARE EARTH COMPLEX, AND LIGHT-EMITTING ELEMENT, SECURITY MEDIUM AND LIGHTING DEVICE USING THE SAME

(75) Inventors: Hiroki Iwanaga, Yokohama (JP); Fumihiko Aiga, Yokohama (JP); Takahiro Sato, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 999 days.

(21) Appl. No.: 12/124,786

(22) Filed: May 21, 2008

(65) Prior Publication Data

US 2008/0303426 A1 Dec. 11, 2008

(30) Foreign Application Priority Data

May 31, 2007 (JP) ................................. 2007-145530

(51) Int. Cl.
*C09K 11/06* (2006.01)
*H01L 51/54* (2006.01)

(52) U.S. Cl. ........ 428/690; 428/917; 313/504; 313/506; 252/301.16; 257/40; 257/102; 257/E51.041; 534/16; 556/21

(58) Field of Classification Search .......... None
See application file for complete search history.

(56) References Cited

U.S. PATENT DOCUMENTS

| 7,147,801 B2 * | 12/2006 | Kozee et al. ............ 252/301.16 |
| 7,250,117 B2 | 7/2007 | Iwanaga et al. |
| 2003/0144487 A1 * | 7/2003 | Grushin et al. ................. 534/15 |
| 2005/0011405 A1 * | 1/2005 | Ikeda et al. ................ 106/31.32 |
| 2007/0236129 A1 | 10/2007 | Iwanaga et al. |

FOREIGN PATENT DOCUMENTS

JP 2003-081986 3/2003

OTHER PUBLICATIONS

Kapoor et al. "Molecular interactions of diaryl and dicyclohexyl phosphine oxides with some lanthanide(III) chlorides." Inorg. Chima. Acta, vol. 110, 1985. pp. 63-68.*

* cited by examiner

*Primary Examiner* — Jennifer Chriss
*Assistant Examiner* — Michael H Wilson
(74) *Attorney, Agent, or Firm* — Turocy & Watson, LLP

(57) ABSTRACT

The present invention provides a fluorescent rare earth complex having high solubility to a medium, showing fluorescence of high intensity and possessing excellent durability, and also provides a light-emitting element using that complex. The rare earth complex comprises a rare earth ion and a phosphine oxide ligand, and the phosphine oxide ligand contains a phosphorus atom connecting to at least one phenyl group. In the phenyl group, at least one of the meta-positions is substituted. It is also necessary that the para-position of the phenyl group be not substituted.

7 Claims, 1 Drawing Sheet

FLUORESCENT RARE EARTH COMPLEX, AND LIGHT-EMITTING ELEMENT, SECURITY MEDIUM AND LIGHTING DEVICE USING THE SAME

CROSS-REFERENCE TO RELATED APPLICATIONS

This application is based upon and claims the benefit of priority from the prior Japanese Patent Applications No. 145530/2007, filed on May 31, 2007; the entire contents of which are incorporated herein by reference.

BACKGROUND OF THE INVENTION

1. Field of the Invention

The present invention relates to a fluorescent rare earth complex showing a high luminous intensity and having a long service life. The invention also relates to a light-emitting medium, a security medium and a lighting device using that complex.

2. Background Art

In recent years, light emitting elements have been improved significantly in luminous intensity and service life, and the market thereof is developing in a wide range around the use for lighting.

Light-emitting diode elements (hereinafter, referred to as "LED elements") using inorganic fluorescent substances, which are mainly used at present, are becoming remarkably improved in emission efficiency, and hence it is said that white LED elements, particularly, will surpass fluorescent lamps in emission efficiency in the future. However, when LED elements are used in lighting devices, the devices are often used in applications requiring that the elements be excellent in color rendering property as well as in emission efficiency. In spite of that, at present, LED elements using only inorganic fluorescent substances cannot satisfy all the required properties.

It is an already known idea to use organic fluorescent substances in LED elements. Actually, however, LED elements using organic fluorescent substances as luminous bodies are not yet practically used for lighting because of the following reasons.

1) Particularly in the case where organic fluorescent substances are employed in a LED element composed of R, G and B luminous bodies and a near ultraviolet LED light source (which is currently becoming mainly used), the fluorescent organic compounds deteriorate seriously by ultraviolet rays. This is because organic compounds are generally poor in durability against ultraviolet rays. Especially if the compound has an $n-\pi^*$ transition absorption band in the near ultraviolet region, the deterioration proceeds rapidly.

2) Organic fluorescent substances often vary their fluorescence spectra according to the concentration, and hence it is difficult to control the spectra. Further, the intensity of the fluorescence also depends upon the concentration, and concentration quenching often occurs in a high concentration range.

3) The fluorescence spectra are also varied according to the kinds of polymers dispersing the organic fluorescent substances.

As compared with the normal organic fluorescent substances, fluorescent substances of rare earth complexes generally have the following advantages.

1) The luminescence wavelength is essentially ascribed to specific characteristics of the rare earth, and hence is not affected by the dye concentration and the kinds of dispersing polymers. Accordingly, the fluorescent substance exhibits a stable fluorescence spectrum.

2) Although the complex has ligands derived from organic compounds, the organic ligands excited by absorbing light are soon deactivated to the ground state because of energy transfer to the center element. Accordingly, the opportunity for causing irreversible chemical reactions in the excited state is reduced enough to expect satisfying durability against ultraviolet rays.

However, in order to develop the general lighting market, it is required further to improve the luminous intensity and the service life.

As a property greatly affecting the durability, stability of ligands to photochemical reactions can be mentioned. The fluorescent substances irradiated with light of LED are exposed to severe conditions such as strong light and heat, and accordingly the radical (oxidative) deterioration is liable to proceed. If the ligand undergoes a chemical reaction, its coordinating ability is lowered to result in elimination of the ligand and, consequently, the fluorescence intensity is often weakened or the denatured ligand may cause deactivation.

On the other hand, in order to obtain a high luminous intensity, the fluorescent complex is required to be solved well in resin. If the solubility is so poor that the fluorescent substance in the form of particles remains in the resin, emitted light is scattered to lower the luminous intensity. For the purpose of improving the solubility, the structure of the fluorescent substance is studied. For example, JP-A-2003-81986 (KOKAI) discloses a complex comprising phosphine oxide ligands in which all the hydrogen atoms of phenyl groups are replaced with fluorine atoms. However, as far as the present inventors know, there is room for improvement in view of the emission intensity although the disclosed complex is improved in solubility.

SUMMARY OF THE INVENTION

According to the present invention, there is provided a rare earth complex comprising a rare earth ion and a phosphine oxide ligand; wherein said phosphine oxide ligand contains a phosphorus atom connecting to at least one phenyl group the para-position of which is not substituted but at least one of the meta-positions of which is substituted with a substituent selected from the group consisting of an alkyl group containing 1 to 20 carbon atoms, a perfluoroalkyl group containing 1 to 20 carbon atoms, an alkoxy group containing 1 to 20 carbon atoms, phenyl, biphenyl, naphthyl, a heterocyclic group, and a substituted group thereof; hydroxyl and a halogen atom.

According to the present invention, there is also provided a fluorescent medium comprising the above rare earth complex dissolved in a polymer.

According to the present invention, there is also provided an organic electroluminescence element comprising a luminescent layer containing the above rare earth complex.

According to the present invention, there is also provided a light-emitting diode element comprising a fluorescent layer containing the above rare earth complex.

Yet further, according to the present invention, there is provided a security medium which is prepared by printing a substrate with a polymer containing the above rare earth complex dissolved therein.

Still furthermore, according to the present invention, there is provided a lighting device compriing the above rare earth complex as a luminescent layer.

DETAILED DESCRIPTION OF THE INVENTION

Figure 1:
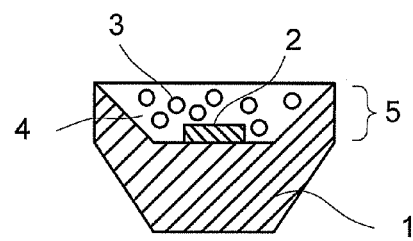
FIG. 1 is a cross-sectional view schematically illustrating the structure of a LED device according to one embodiment of the present invention.

The rare earth complex according to the present invention comprises a rare earth ion and a phosphine oxide ligand. The phosphine oxide ligand contains a P=O bond in the structure, and is coordinated to the rare earth ion through the P=O bond. The phosphorus atom at the center of the ligand can be combined with various substituents, but in the present invention the phosphorus atom connects to at least one phenyl group having a substituent at the meta-position.

It is an important characteristic of the invention that a phenyl group in the phosphine oxide ligand has a substituent at the meta-position. The rare earth complex containing such particular phosphine oxide ligand is improved in saturation solubility to a medium such as a polymer or a solvent while the fluorescence intensity and the durability are scarcely changed. However, if the phenyl group also has a substituent at the para-position, the above effect cannot be obtained. It is, therefore, important that the para-position is not substituted, namely, that a hydrogen atom is attached at the para-position.

If the phenyl group has a substituent at the para-position, the fluorescence intensity and the durability are liable to decline although the rare earth complex has improved saturation solubility. The reason of this is not clear at present. However, it can be understood that, if the para-position is substituted, the saturation solubility is improved because of steric hindrance but the electronic state is so changed that the energy transfer from the ligand to the rare earth ion is inhibited to lower the efficiency of the energy transfer and consequently to weaken the fluorescence intensity and to impair the durability.

On the other hand, it can be also understood that, if the meta-position is substituted, the saturation solubility is more improved because of steric hindrance than that in the case where the para-position is substituted and the electronic state is not so changed as to inhibit the energy transfer, and consequently the fluorescence intensity is enhanced and the durability is improved.

In consideration of the above, the substituent at the meta-position of the phenyl group is supposed to give physical effects rather than electronic effects. From this viewpoint, the structure of the substituent can be widely selected. The substituent is preferably selected from the group consisting of an alkyl group containing 1 to 20 carbon atoms, a perfluoroalkyl group containing 1 to 20 carbon atoms, an alkoxy group containing 1 to 20 carbon atoms, phenyl, biphenyl, naphthyl, a heterocyclic group, and a substituted group thereof; hydroxyl and a halogen atom. Among the above, the halogen atom, the alkyl group, the perfluoroalkyl group or the alkoxy group is particularly preferred. The alkyl group, the perfluoroalkyl group or the alkoxy group may have a straight-chain, branched-chain or cyclic structure, and the number of carbon atoms is more preferably 1 to 8. The halogen atom is preferably fluorine, chlorine or iodine. In the case where hydroxyl is adopted as the substituent, it must be noted that the hydroxyl may cause a chemical reaction.

The phenyl group contained in the phosphine oxide ligand has two meta-positions, and at least one of them must be substituted and both may be substituted. In the present invention, it is also necessary that the para-position of the phenyl group be not substituted and further it is preferred that the ortho-position be not substituted, either. This is because the substituent at the ortho-position may also give unfavorable electronic effects to lower the fluorescence intensity.

The phosphine oxide ligand can contain two or more phenyl groups, but the effect of the present invention can be obtained as long as at least one of the meta-positions of at least one phenyl group is substituted. Accordingly, various substituents can be combined with the phosphorus atom in the phosphine oxide ligand. However, the phosphorus atom is preferably combined with only a few kinds of the substituents since that ligand can be readily prepared.

The rare earth complex according to the present invention preferably also contains a ligand other than the phosphine oxide ligand. The ligand other than the phosphine oxide ligand, such as a β-diketone ligand or a sulfonyl amide ligand, causes distortion of the ligand field, and thereby the fluorescence intensity is apt to increase. The rare earth complex containing two or more kinds of phosphine oxide ligands is also apt to emit fluorescence of increased intensity because of the distorted ligand field. In particular, the aforementioned aromatic phosphine oxide ligand, which comprises a phosphorus atom connecting to a phenyl group having a substituent at the meta-position, in combination with an aliphatic phosphine oxide ligand, which comprises a phosphorus atom connecting to an aliphatic substituent, remarkably enhances the fluorescence intensity, and therefore that combination is preferred.

The rare earth complex is preferably represented by one of the following formulas (1) to (4):

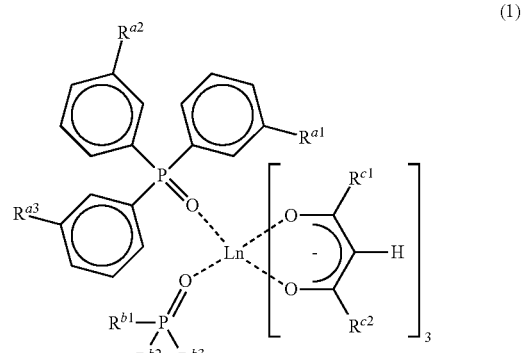

(1)

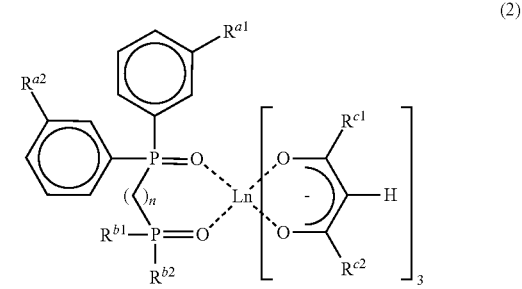

(2)

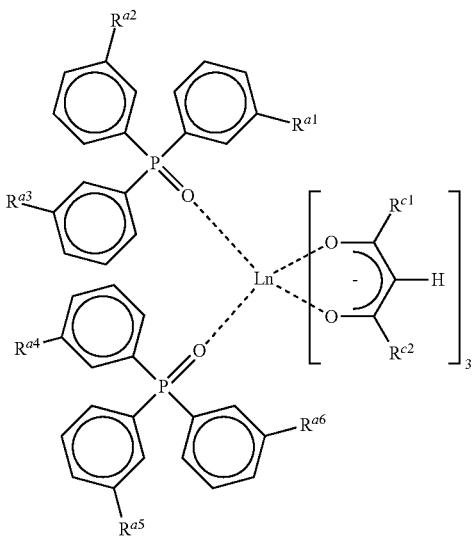

(3)

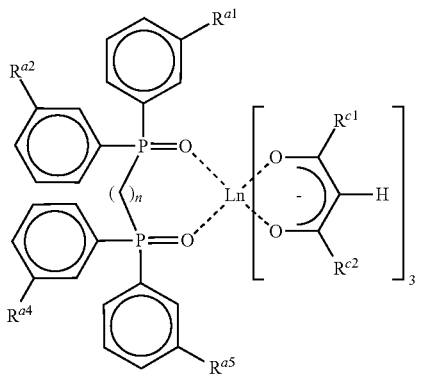

(4)

wherein $R^{a1}$ to $R^{a6}$, $R^{b1}$ to $R^{b3}$ and $R^{c1}$ to $R^{c3}$ may be the same or different form each other; each of them independently is a substituent selected from the group consisting of hydroxyl, a halogen atom, an alkyl group containing 1 to 20 carbon atoms, a perfluoroalkyl group containing 1 to 20 carbon atoms, an alkoxy group containing 1 to 20 carbon atoms, phenyl, biphenyl, naphthyl, a heterocyclic group, and a substituted group thereof; n is an integer of 1 to 7, and Ln is a rare earth ion. Preferably, $R^{a1}$ to $R^{a6}$ are individually the halogen atom, the alkyl group, the perfluoroalkyl group or the alkoxy group.

In the present invention, the rare earth ion can be selected according to the uses so that fluorescence at a suitable wavelength can be obtained. The rare earth ion, however, is preferably a lanthanide ion, more preferably a europium or terbium ion. In order to obtain a fluorescent rare earth complex excellent in color rendering property, the rare earth ion is preferably a europium ion because it shows a large spectrum in the red region.

The rare earth complex according to the present invention has large saturation solubility to a medium such as a solvent or a polymer. Accordingly, for example, the rare earth complex is dissolved in a polymer to prepare a fluorescent medium which is colorless and transparent under room light but which emits intense fluorescence under ultraviolet light or external light in the near ultraviolet region. The rare earth complex, therefore, can be applied to various ornaments and security systems. In the case where the rare earth complex is used in a security system, for example, the complex is dissolved in a polymer to prepare a fluorescent medium, with which a bar code is printed on a security card to produce a security medium. The security medium thus obtained is completely colorless under visible light, but emits intense fluorescence under ultraviolet light. In the security system using that medium, it is difficult to recognize even whether the bar code is printed or not, so that high security is ensured.

The fluorescent medium comprising the rare earth complex according to the present invention dissolved in a polymer or the like is excellent in the durability and in the emission intensity, and hence it can be suitably used for light-emitting devices which comprises a light emitting element and a luminescent medium formed on the light emitting element. In the present invention, the light emitting elements involves, for example, a light emitting diode (LED) elements and an organic electroluminescence (EL) elements which comprises an electroluminescent layer emitting light when a fluorescent substance is excited by injection of carrier from an electrode.

Examples of the light-emitting devices include a near ultraviolet light-emitting red LED device, and FIG. 1 shows a cross sectional view thereof. In FIG. 1, an LED chip 2 is provided on a storage vessel 1, and a fluorescent layer 5 comprising a matrix polymer 4 and a therein-dispersed fluorescent complex 3 according to the present invention is placed on the LED chip 2. In this constitution, the fluorescent complex shows fluorescence when irradiated with light emitted from the LED chip. If other fluorescent layers are further provided, a white LED device can be obtained.

In the light-emitting device, a fluororesin is preferably used as a resin constituting the fluorescent layer since it contains C—H bonds and O—H bonds in relatively small amounts. Accordingly, resins having high fluorination degrees are more preferably used. However, the resin is properly selected in consideration of various conditions such as solubility and dispersability of the fluorescent complex and other adopted components. Examples of the usable resins include: Cefral Coat FG700X, A402B, A610X, manufactured by Central Glass Co., Ltd.; Lumiflon manufactured by Asahi Glass Co., Ltd.; Zeonor manufactured by Zeon Corporation; KYNAR, KYNAR FLEX manufactured by Atofina Japan K.K.; Dufron manufactured by Nippon Paint Co., Ltd.; and Dyneon THV220, 310 and 415 (all the above products being trademarks) manufactured by Sumitomo 3M Limited. The fluorescent layer can contain not only the fluorescent complex according to the present invention but also other fluorescent substances such as YAG fluorescent substance, alkaline earth metal silicate fluorescent substances, alkaline earth metal phosphate fluorescent substances, halophosphate fluorescent substances, BAM:Eu,Mn, BAM:Eu, ZnS, $SrGa_2S_4$:Eu, oxynitride:Eu, $SrAlO_4$:Eu, alkaline earth apatite: Eu, Ca apatite: Eu,Mn, CaS:Ce, $Y_2SiO_5$:Tb, $Sr_2P_2O_7$:Eu,Mn, and $SrAl_2O_4$:Eu. Some of the above fluorescent substances can be used in combination to obtain white luminescence.

The organic EL element according to the present invention comprises the aforementioned rare earth complex as a dopant. There is no particular restriction on the host material, but the host material is preferably at least one selected from the group consisting of aromatic amine derivatives, carbazole derivatives, and thiophene oligomers and polymers.

Figure 2:
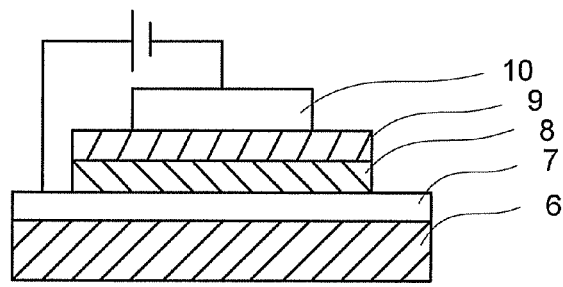
FIG. 2 is a cross-sectional view schematically illustrating the structure of an organic electroluminescence (EL) element according to one embodiment of the present invention.

FIG. 2 shows an example of the constitution of the organic EL element according to the present invention. The organic EL element shown in FIG. 2 is composed of an anode 7 comprising a glass substrate 6 and ITO, a luminescent layer 8, an electron transport layer 9, and a cathode 10. In addition, other layers such as a hole transport layer, a hole injection layer and a hole blocking layer can be optionally provided in combination.

The anode in the organic EL element according to the present invention is made of, for example, gold, copper iodide, tin oxide or indium tin oxide (ITO). Examples of materials for the cathode include metals of the groups 1 and 2 in the periodic table, such as sodium, lithium, magnesium and calcium; and metals of the group 3 such as gallium and indium. Examples of the hole transfer materials include arylamine derivatives, carbazole derivatives, thiophene oligomers and polymers, and copper phthalocyanine. The hole transfer material can be used as the host material, in which the rare earth complex is dispersed as the dopant, to form the luminescent layer. Examples of the hole injection material include copper phthalocyanine.

The rare earth complex according to the present invention can be directly used in the luminescent layer, and in addition the rare earth elements are also usable as the dopant in the hole transfer material.

Further, the luminescent layer can also contain $Alq_3$ as Al oxine complexes, perylene compounds, naphthalene compounds, coumarin compounds, oxadiazole compounds, aldazine compounds, bisbenzoxazoline compounds, bisstyryl compounds, pyradine compounds, CPD compounds, In oxine complexes, Zn complexes, Fe oxine complexes, and Ga imine complexes. It is necessary that the material of the hole blocking layer have large ionization potential and small hole-transferability, and examples of the material include triazole compound and derivatives thereof. Examples of materials for the electron transfer layer include metal chelate compounds including $Alq_3$, benzoxadole, benzothiazole, tris (8-hydroxyquinolinol)bismuth, and perylene compounds.

Figure 3:
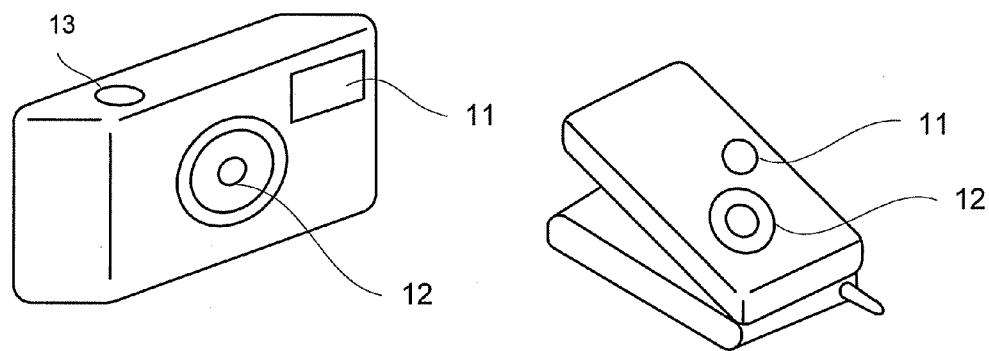
FIG. 3 is a conceptual sketch illustrating a camera equipped with a flashing device using a fluorescent complex according to one embodiment of the present invention.
Figure 4:
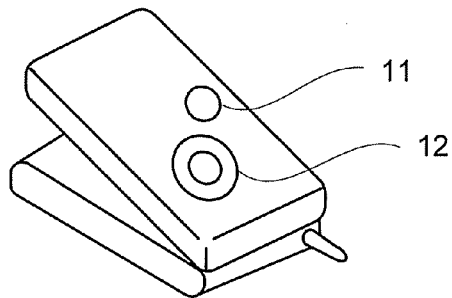
FIG. 4 is a conceptual sketch illustrating a cellular phone with a camera, the camera comprising a flashing device using a fluorescent complex according to one embodiment of the present invention.

The above light-emitting element per se can be used in a lighting device, and further can be also applied to a flashing device utilizing a short emission life. The light-emitting element according to the present invention employs a chip consuming small electric energy such as LED, and hence can be advantageously used as a flashing device of a camera installed in a cellular phone. In that application, the light-emitting element according to the present invention can be used in the same manner as other conventional light-emitting elements. FIGS. 3 and 4 are conceptual sketches illustrating a camera equipped with a flashing device and a cellular phone with a camera, respectively. The flashing device installed in each camera uses a fluorescent complex according to one embodiment of the present invention.

The camera and the cellular phone shown in FIGS. 3 and 4 individually comprise a flashing device 11, a lens 12, and a shutter button 13 (not shown in FIG. 4), and their constitutions are the same as those of the conventional camera and cellular phone. However, the flashing device 11 comprises the light-emitting element according to the present invention, which can be advantageously used because of excellent color rendering property and a long service life.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

EXAMPLES

The present invention is further explained by the following examples, but they by no means restrict the present invention.

Example 1

A europium complex represented by the following formula (5) was synthesized.

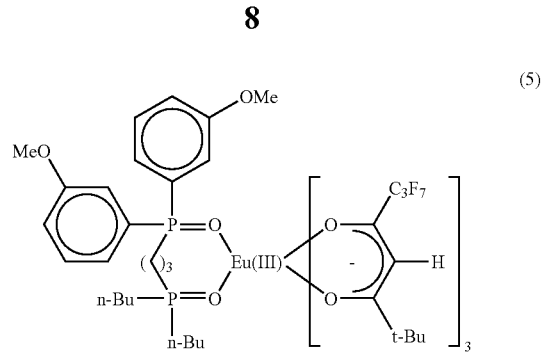

With respect to the complex thus prepared, the saturation solubility, the fluorescent intensity and the durability were measured to obtain satisfying results shown in Table 1.

Comparative Example 1

A europium complex represented by the following formula (6) was synthesized.

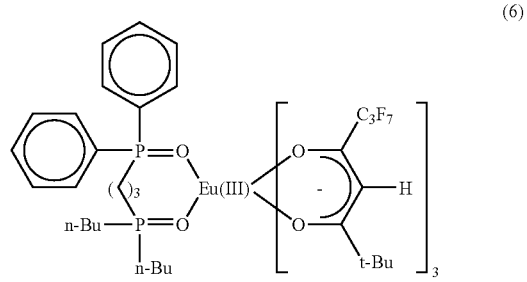

With respect to the complex thus prepared, the saturation solubility, the fluorescent intensity and the durability were measured, and as a result it was found that the fluorescent intensity and the durability were satisfying but the saturation solubility was not.

Comparative Example 2

A europium complex represented by the following formula (7) was synthesized.

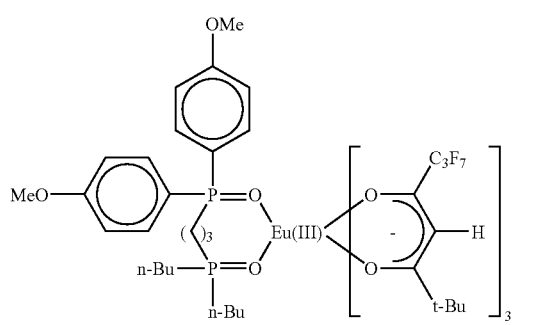

With respect to the complex thus prepared, the saturation solubility, the fluorescent intensity and the durability were measured, and as a result it was found that the saturation solubility was satisfying but the fluorescent intensity and the durability were not.

Example 2

A europium complex represented by the following formula (8) was synthesized.

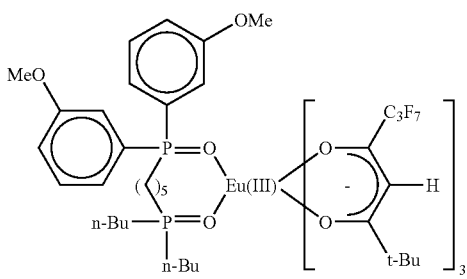

(8)

With respect to the complex thus prepared, the saturation solubility, the fluorescent intensity and the durability were measured to obtain satisfying results shown in Table 1.

Comparative Example 3

A europium complex represented by the following formula (9) was synthesized.

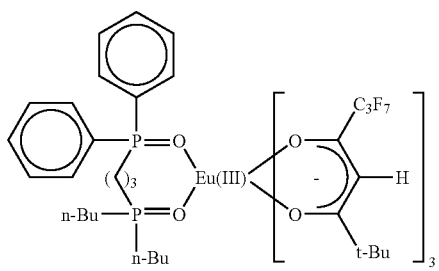

(9)

With respect to the complex thus prepared, the saturation solubility, the fluorescent intensity and the durability were measured, and as a result it was found that the fluorescent intensity and the durability were satisfying but the saturation solubility was not.

Comparative Example 4

A europium complex represented by the following formula (10) was synthesized.

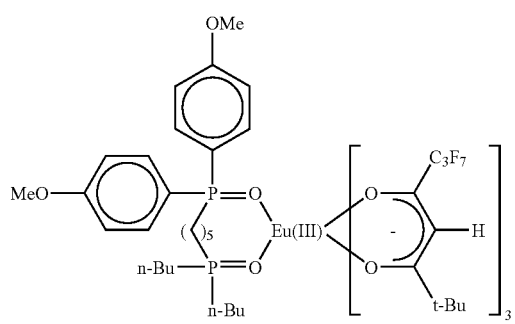

(10)

With respect to the complex thus prepared, the saturation solubility, the fluorescent intensity and the durability were measured to obtain results shown in Table 1.

Example 3

A fluorescent polymer containing 20 wt. % of the europium complex represented by the formula (5) dissolved in a fluororesin Cefral 220 (manufactured by Central Glass Co., Ltd.) was prepared. A fluorescent layer made of the fluorescent polymer thus obtained was placed on a LED chip giving a luminescence centered at 402 nm, to produce a LED element. The constitution of the LED element was shown in FIG. 1. An electric current of 20 mA was made to flow into the LED element, to obtain a luminous intensity of 220 mcd. Even after the LED element kept lighting for 200 hours, the luminous intensity was not weakened.

Comparative Example 5

The procedure of Example 3 was repeated, except that the compound represented by the formula (6) was used as the europium complex to obtain a LED element. The LED element thus obtained exhibited a small luminous intensity of 120 mcd. Even after the LED element kept lighting for 200 hours, the luminous intensity was not weakened.

Comparative Example 6

The procedure of Example 3 was repeated, except that the compound represented by the formula (7) was used as the europium complex to obtain a LED element. The LED element thus obtained exhibited a very small luminous intensity of 10 mcd.

Example 4

An EL element comprising a luminescent layer and an electron transfer layer was produced. The luminescent layer contained a fluorescent substance represented by the formula (5) in Example 1 as the guest and a compound represented by the following formula (11) as the host, and the electron transfer layer was composed of a compound having a structure represented by the following formula (12):

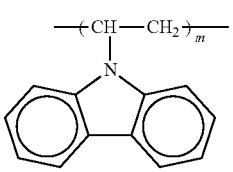

(11)

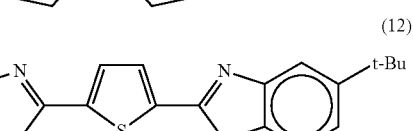

(12)

wherein m is an integer of 1 or more.

A voltage of 12 V was applied between the electrodes, to obtain a luminance (brightness) of 180 cd/m². In the continuous lighting test (for durability), it took 40,000 hours for the luminance to be reduced to half. The result was satisfying.

Comparative Example 7

The procedure of Example 4 was repeated, except that the compound represented by the formula (7) was used as the host material of the luminescent layer, to produce an EL element. The luminance was measured in the same manner and found to be 20 cd/m², which was too poor to use practically.

Example 5

The fluorescent substance represented by the formula (5) was dissolved in Cefral 220 (manufactured by central Glass Co., Ltd.) in 20 wt. %, to form a film. The film had no viewability under room light, but emitted a luminescence of 800 lm at the maximum when irradiated with ultraviolet light.

Comparative Example 8

The procedure of Example 5 was repeated, except that the fluorescent substance of the formula (7) was used to form a film. The film had no viewability under room light, but emitted a weak luminescence when irradiated with ultraviolet light.

Example 6

A europium complex represented by the following formula (13) was synthesized.

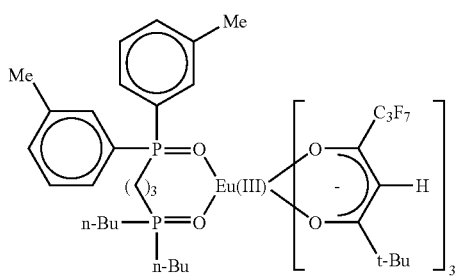
(13)

With respect to the complex thus prepared, the saturation solubility, the fluorescent intensity and the durability were measured to obtain satisfying results shown in Table 1.

Example 7

A europium complex represented by the following formula (14) was synthesized.

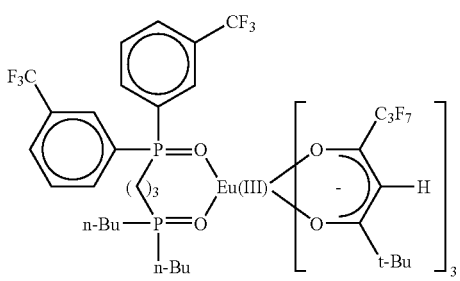
(14)

With respect to the complex thus prepared, the saturation solubility, the fluorescent intensity and the durability were measured to obtain satisfying results shown in Table 1.

Example 8

A europium complex represented by the following formula (15) was synthesized.

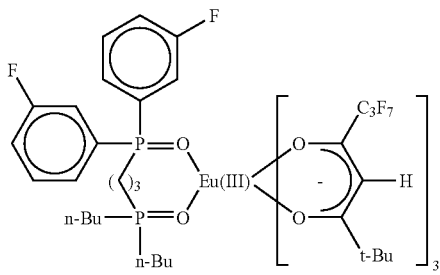
(15)

With respect to the complex thus prepared, the saturation solubility, the fluorescent intensity and the durability were measured to obtain satisfying results shown in Table 1.

Example 9

A terbium complex represented by the following formula (16) was synthesized.

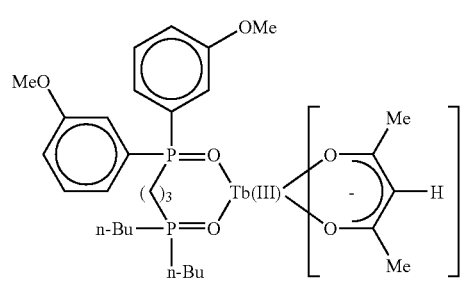
(16)

With respect to the complex thus prepared, the saturation solubility, the fluorescent intensity and the durability were measured to obtain satisfying results shown in Table 1.

TABLE 1

| | Rare earth complex | Saturation solubility (Eu: µg/g) | Fluorescence intensity (616 nm, a.u.) | Durability (hours) |
|---|---|---|---|---|
| Example 1 | (5) | 500 | 1505 | 2000 |
| Comp. Ex. 1 | (6) | 110 | 1696 | 1900 |
| Comp. Ex. 2 | (7) | 330 | 12 | 24 |
| Example 2 | (8) | 40 | 1810 | 3000 |
| Comp. Ex. 3 | (9) | 3.1 | 1600 | 2500 |
| Comp. Ex. 4 | (10) | 90 | 9 | 48 |
| Example 6 | (13) | 450 | 1600 | 1800 |
| Example 7 | (14) | 600 | 2100 | 2300 |
| Example 8 | (15) | 400 | 1550 | 1900 |
| Example 9 | (16) | 200 | 850 | 1500 |

Remarks)
Saturation solubility: Solubility to a fluorinated solvent (Vertrel XF [trademark], manufactured by DuPont U.S.).
Durability: Time to reduce the fluorescence intensity to half under the condition that a film formed from a 20% solution of the complex dissolved in Cefral 220 [trademark] manufactured by central Glass Co., Ltd. was left at a temperature of 85° C. and a humidity of 85%.

The invention claimed is:
1. A rare earth complex comprising:
a lanthanide ion (Ln),
a phosphine oxide ligand, and
a β-diketone ligand or a sulfonyl amide ligand,
wherein the rare earth complex is represented by one of complex (2) or complex (4)

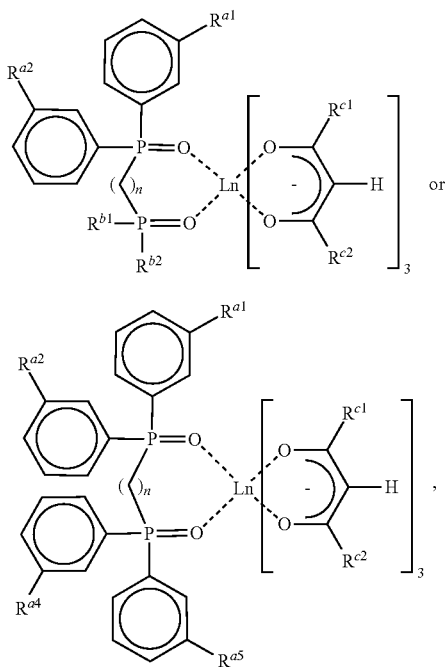

wherein $R^{a1}$, $R^{a2}$, $R^{a4}$ and $R^{a5}$, $R^{b1}$ and $R^{b2}$ and $R^{c1}$ and $R^{c2}$ are the same or different substituents selected from a group consisting of hydroxyl, a halogen atom, an alkyl group containing 1 to 20 carbon atoms, a perfluoroalkyl group containing 1 to 20 carbon atoms, an alkoxy group containing 1 to 20 carbon atoms, phenyl, biphenyl, naphthyl, a heterocyclic group, and a substituted group thereof and n is an integer of 1 to 7, wherein said phosphine oxide ligand contains a phosphorus atom connecting to at least one phenyl group the para-position of which is not substituted but at least one of the meta-positions of which is substituted with a substituent selected from the group consisting of an alkyl group containing 1 to 20 carbon atoms, a perfluoroalkyl group containing 1 to 20 carbon atoms, an alkoxy group containing 1 to 20 carbon atoms, phenyl, biphenyl, naphthyl, a heterocyclic group, and a substituted group thereof; hydroxyl and a halogen atom.

2. The rare earth complex according to claim 1, wherein said lanthanide ion is a europium or terbium ion.

3. A fluorescent medium comprising the rare earth complex according to claim 1 dissolved in a polymer.

4. An organic electroluminescence element comprising a luminescent layer containing the rare earth complex according to claim 1.

5. A light-emitting diode element comprising a fluorescent layer containing the rare earth complex according to claim 1.

6. A security medium prepared by printing a substrate with a polymer containing the rare earth complex according to claim 1 dissolved therein.

7. A lighting device using the rare earth complex according to claim 1 as a luminescent layer.

* * * * *